United States Patent
Durden et al.

(10) Patent No.: US 6,251,950 B1
(45) Date of Patent: Jun. 26, 2001

(54) ALIPHATIC PROPARGYLAMINES AS CELLULAR RESCUE AGENTS

(75) Inventors: David Durden; Alick Paterson; Bruce Davis; Lillian Dyck; Peter Yu; Xinmin Li; Alan Boulton, all of Saskatchewan (CA)

(73) Assignee: University of Saskatchewan, Saskatoon (CA)

( * ) Notice: Subject to any disclaimer, the term of this patent is extended or adjusted under 35 U.S.C. 154(b) by 0 days.

(21) Appl. No.: 09/110,548

(22) Filed: Jul. 6, 1998

Related U.S. Application Data

(62) Division of application No. 08/891,904, filed on Jul. 14, 1997, now Pat. No. 5,840,979.

(51) Int. Cl.$^7$ .................................................. A61K 31/13
(52) U.S. Cl. ........................................ 514/671; 564/504
(58) Field of Search .............................. 514/671; 564/509

(56) References Cited

U.S. PATENT DOCUMENTS

| | | | |
|---|---|---|---|
| 5,169,868 | 12/1992 | Yu et al. | 514/671 |
| 5,436,273 | * 7/1995 | Salvador et al. | 514/671 |

OTHER PUBLICATIONS

Casonline printout 1976:405145 and 1974:490969, 1976/1974.*
Chem Abstracts 1967: 104673, Boissier et al 1967.*
Yoshida et al., *Xenobiotica*, 162(2), 129–136 (1986).
Yu et al., *J. Neurochemistry*, 63(5), 1820–1828 (1994).
Yu et al., *N. Neurochemistry*, 62(2)(, 697–704 (1994).
Yu et al., *J. Medicinal Chemistry*, 35(20), 3705–3713 (1992).
Yoles et al., *Society for Neuroscience*, 21, 562, Abstract 230.18 (1995).
Tatton et al., *Neurology*, 47(3), S171–S183 (1996).
Wu et al., *J. Neural Transm.*, 100, 53–61 (1995).
Tatton et al., *J. Neurochemistry*, 63(4), 1572–1575 (1994).
Tatton et al., *J. Neuroscience Research*, 30(4), 666–672 (1991).
Salo et al., *J. Neuroscience Research*, 31, 394–400 (1992).
Paterson et al., *Society for Neuroscience*, 23, Abstract 880.6 (1997).
Rideout et al., *Society for Neuroscience*, 23, Abstract 34.4 (1997).
Paterson et al., *J. Neurochemistry*, (in press) (1997).
Oh et al., *J. Neuroscience Research*, 38, 64–74 (1994).
Paterson et al., *Neuroscience and Biobehavioral Reviews*, 20, 1–6 (1996).
Mytilineou et al., *J. Neurochemistry*, 68(1), 434–436 (1997).
Mytilineou et al., *J. Neurochemistry*, 68(1), 33–39 (1997).
Knollema et al., *Stroke*, 26(10), 1883–1887 (1995).
Lai et al., *Toxicology and Applied Pharmacology*, 142, 186–191 (1997).
Grace et al., *Chem. Res. Toxicol.*, 7, 286–290 (1994).
Finberg et al., *J. Neural Transm.*, 48, 95–101 (1996).
Davis et al., *American Society for Neurochemistry* (Mar. 1995) (Abstract).
Boissier et al., *Therapie*, XXII, 367–373 (1967) (See English Summary on p. 373).
Berry et al., *Progress in Neurobiology*, 44, 141–161 (1994).
Ansari et al., *J. Neuroscience*, 13(9), 4042–4053 (1993).

* cited by examiner

Primary Examiner—Samuel Barts
(74) Attorney, Agent, or Firm—Synnestvedt & Lechner LLP

(57) ABSTRACT

The present invention relates to the use of a group of propargylamines of the general formula (I)

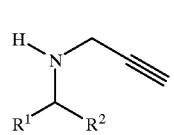

(I)

wherein $R^1$ is hydrogen or $CH_3$ and $R^2$ is $(CH_2)_n CH_3$ and n is an integer from 0 to 16, and salts thereof, as cellular rescue agents in the treatment and prevention of diseases in which cell death occurs by apoptosis. Some of the compounds of formula I are novel. The invention is also directed to the use of these compounds in the treatment of these diseases, as well as to processes for the preparation of the compounds.

8 Claims, 2 Drawing Sheets p < 0.05 compared to ara C alone

ALIPHATIC PROPARGYLAMINES AS CELLULAR RESCUE AGENTS

CROSS-REFERENCE TO RELATED APPLICATIONS

This is a divisional application of U.S. application Ser. No. 08/891,904, filed Jul. 14, 1997, now U.S. Pat. No. 5,840,979, issued Nov. 24, 1998.

FIELD OF THE INVENTION

The invention relates to a class of propargylamines, their salts and to pharmaceutical compositions containing such compounds. The compounds have cellular rescue properties which make them useful in the treatment and prevention of diseases in which cell death occurs by apoptosis.

BACKGROUND OF THE INVENTION

Neurodegenerative disorders of both acute types (e.g. stroke, head trauma, Bell's palsy, spinal cord and other nerve crush injuries) and chronic types (e.g. Alzheimer's disease, Parkinson's disease, Picks's disease, amyotrophic lateral sclerosis, Huntington's disease, glaucoma, as well as idiopathic neuropathies) are responsible for enormous human suffering, are a burden on health care systems and result in significant economic loss. A drug or treatment which could prevent, delay or alleviate one or more of these conditions would be of immense value.

R-Deprenyl hydrochloride (selegiline, L-deprenyl) has been demonstrated to be an effective adjuvant to L-dopa in the treatment of Parkinson's disease and, in early otherwise untreated cases, it has more recently been reported to delay onset of symptoms when administered alone. It has also been claimed that the use of deprenyl improved the clinical condition of some Alzheimer patients and the symptoms of attention deficit disorder in Tourette's syndrome patients. In addition, it has been observed to prolong life span and sexual activity in rodents and humans.

Initially, the improvement in Parkinson's and other patients was ascribed to the protection of neurons by the MAO-B inhibitory properties of deprenyl. However, studies of the effect of deprenyl on neuronal survival in N-methyl-4-phenyl-1,2,3,6-tetrahydro-pyridine (MPTP)-induced Parkinsonism, axotomized immature facial motoneurons in rats, and hippocampal neuron death following ischemia or excitotoxin insult have shown that survival is increased by a mechanism which is independent of monoamine oxidase type B (MAO-B) inhibition. Studies with PC12 cells have shown that deprenyl can prevent apoptosis by a mechanism which involves selective alterations in gene expression to block the loss of mitochondrial function which in turn would commit these cells to apoptosis. Deprenyl has also been shown to prevent N-(2-chloroethyl)-N-ethyl-2-bromobenzylamine (DSP-4)-induced degeneration of rat brain noradrenergic axons and terminals. The concentrations of deprenyl required to prevent apoptosis are at least an order of magnitude lower than the minimum necessary for MAO-B inhibition in some of these models. Furthermore, not all MAO-B inhibitors are effective in rescuing damaged neurons.

Deprenyl is metabolized to amphetamine and methamphetamine which have been observed to be neurotoxic even at quite low concentrations, which creates a possible problem with deprenyl as a neuronal rescue drug. Similarly deprenyl has been shown to enhance the cytotoxicity of dopamine towards catecholaminergic neuroblastoma SH-SY5Y cells. Deprenyl has been demonstrated to be a substrate for cytochrome P450 enzymes, which mediate the dealkylation process leading to the observed metabolites, methamphetamine and desmethyldeprenyl. Desmethyldeprenyl is active as an anti-apoptotic drug and studies involving the inhibition of P450 enzymes have shown that desmethyldeprenyl is the active component when deprenyl is given since pretreatment with a P450 inhibitor such as proadifen eliminates the neurorescue properties of deprenyl. It has also been reported that the desmethyldeprenyl-like compound, N-propargyl-1-aminoindan, is effective in enhancing the in vitro neuronal survival after glutamate toxicity.

Recently, some aliphatic analogues of deprenyl have proven to be as effective MAO-B inhibitors as deprenyl. As with deprenyl, it is the R-enantiomers which are active. They have also been shown to protect and rescue damaged neurons in the same models of neurodegeneration described above for deprenyl.

The aliphatic propargylamines identified in this application are active as antiapoptotic compounds.

DESCRIPTION OF THE INVENTION

The present invention relates to a group of propargylamines of general formula (I)

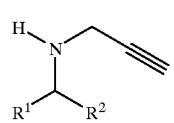

(I)

wherein $R^1$ in hydrogen or $CH_3$ and $R^2$ is $(CH_2)_nCH_3$ and n is 0 or an integer from 1 to 16, preferably 1 to 10, more preferably 1 to 5, and the salts thereof, particularly pharmaceutically acceptable salts.

Compounds of the general formula (I) in which $R^1$ differs from $R^2$ are chiral. It has been found that the R-enantiomers are useful as cellular rescue agents for the treatment and prevention of diseases in which cell death occurs by apoptosis, such as those mentioned above. This effect is observed at doses much lower than those required for MAO-B inhibition. The S-enantiomers do not prevent apoptosis but can antagonise the anti-apoptotic actions of the R-enantiomers, and are useful as research tools. The achiral compounds display cellular rescue properties.

The racemates are useful as intermediates in the preparation of R- and S-enantiomers. Methods of separating racemates are known. Suitable methods include fractional crystallization of a suitable salt, chromatography and preparation of for example N-acetyl derivatives, followed by deacetylation of one enantiomer with a stereospecific enzyme. It is preferred, however, to make chiral compounds of formula (I) from chiral reactants, using reactions that do not destroy the stereochemistry. When referring to enantiomers, it is preferred that an enantiomer shall not contain more than about 3% of the enantiomer of the opposite configuration. It is particularly preferred that an enantiomer contain less than about 1% of the enantiomer of the opposite configuration.

The invention relates as well to the use of compounds of the general formula I, as defined above, and salts thereof, as cellular rescue agents for the treatment and prevention of diseases in which cell death occurs by apoptosis including stroke, head trauma, Bell's palsy, spinal cord and other nerve crush injuries, Alzheimer's disease, Parkinson's disease, Pick's disease, amyotrophic lateral sclerosis, Huntington's disease, multiple sclerosis, cardiac myopathies, nephropathy, retinopathy, diabetic complications, glaucoma, as well as idiopathic neuropathies.

DETAILED DESCRIPTION OF PREFERRED EMBODIMENTS

The present invention relates to a group of propargylamines of general formula (I),

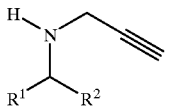
(I)

wherein $R^1$ is hydrogen or $CH_3$ and $R^2$ is $(CH_2)_nCH_3$ where n is an integer from 0 to 16, and salts thereof, and their use as cellular rescue agents for the treatment and prevention of diseases in which cell death occurs by apoptosis, as mentioned above.

Preferred compounds of the invention include:

N-(ethyl)propargylamine;
N-(1-Propyl)propargylamine;
N-(2-Propyl)propargylamine;
N-(1-Butyl)propargylamine;
N-(1-Pentyl)propargylamine;
N-(1-Hexyl)propargylamine;
N-(1-Heptyl)propargylamine;
N-(1-Octyl)propargylamine;
N-(1-Nonyl)propargylamine;
N-(1-Decyl)propargylamine;
N-(1-Undecyl)propargylamine;
N-(1-Dodecyl)propargylamine;
(R)-N-(2-Butyl)propargylamine;
(R)-N-(2-Pentyl)propargylamine;
(R)-N-(2-Hexyl)propargylamine;
(R)-N-(2-Heptyl)propargylamine;
(R)-N-(2-Octyl)propargylamine;
(R)-N-(2-Nonyl)propargylamine;
(R)-N-(2-Decyl)propargylamine;
(R)-N-(2-Undecyl)propargylamine;
(R)-N-(2-Dodecyl)propargylamine;

The S-enantiomers antagonize the effect of the R-enantiomers, and are useful as research tools. Preferred compounds of the S-configuration are:

(S)-N-(2-Butyl)propargylamine;
(S)-N-(2-Pentyl)propargylamine;
(S)-N-(2-Hexyl)propargylamine;
(S)-N-(2-Heptyl)propargylamine;
(S)-N-(2-Octyl)propargylamine;
(S)-N-(2-Nonyl)propargylamine;
(S)-N-(2-Decyl)propargylamine;
(S)-N-(2-Undecyl)propargylamine;
(S)-N-(2-Dodecyl)propargylamine;

Compounds of formula (I) in which $R^1$ is hydrogen and n is 0 or 1 to 4, and the compound in which $R^1$ is $CH_3$ and n is 0 are known. The racemates of compounds of formula (I) in which $R^1$ is $CH_3$ and n is 1 or 4 are also known. It is believed that the other compounds of formula (I) including the enantiomers of compounds in which $R^1$ is $CH_3$ and n is 1 or 4 are novel. It was not previously known that any of the compounds of formula I have cellular rescue properties.

Particularly preferred as cellular rescue agents are those compounds of the R configuration.

The S-enantiomers antagonize the antiapoptotic actions of the R-enantiomers, and are useful as research tools.

The invention extends to salts of compounds of formula I. For administration the salts should be pharmaceutically acceptable, but other salts may be useful, for example, in synthesis or for purification.

Compounds of the invention can be prepared in a variety of different ways. One process involves (a) reacting a primary amine of formula (II)

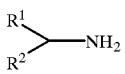
(II)

with a propargyl reactant of formula (III)

$$LCH_2C\equiv CH \quad (III)$$

wherein L is a leaving group, for example a halide or a $(C_1-C_4)$alkylsulphonyl, tosyl or mesyl group. Bromine is preferred.

It is possible to use an amine of the formula (II) in which $R^1$ differs from $R^2$ in the form of a racemate and to separate enantiomers subsequently, but it is preferred to use an amine in substantially enantiomerically pure form. In one preferred embodiment two equivalents of amine are reacted with one equivalent of the compound of formula III, preferably propargyl bromide to form the required propargylamine and the hydrobromide salt of the amine, which can be isolated and reused, in accordance with the following reaction scheme.

Two Equivalents Amine and One Equivalent Propargyl Bromide in Ether:

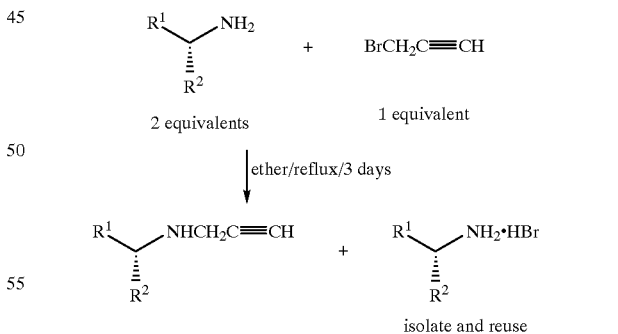

$R^2$=methyl, ethyl, propyl, butyl, pentyl, hexyl, heptyl, octyl, nonyl, decyl;

$R^1$=hydrogen, methyl;

Chiral primary amines (R- and S-forms) were prepared by tartrate recrystallization from methanol, except for the butyl analogue. (R)- and (S)-2-Butylamine were purchased from Aldrich Chemical Co.

Another route to compounds of the invention involves (b) reacting a compound of the formula (IV)

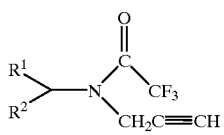
(IV)

wherein $R^1$ and $R^2$ are as defined above, with alcoholic hydroxide, to remove the trifluoroacetyl group.

The compound of formula (IV) can be obtained by a process that involves trifluoroacetylation of the amine, followed by propargylation. Again, the amine can be used in racemic or enantiomerically pure form. The amine is reacted with trifluoroacetic anhydride or a trifluoroacetyl halide in an inert organic solvent, for instance a chlorinated hydrocarbon such as methylene dichloride, chloroform or carbon tetrachloride, and a base, for example an organic base such as triethylamine. The N-trifluoroacetylamine is then refluxed with a propargyl compound of formula (III), suitably in the presence of a base such as potassium t-butoxide in a polar organic solvent, for example acetonitrile, and in the presence of a crown ether, for example 18-crown-6. The product of this reaction is then hydrolysed, suitably by reaction with a base such as an alkali metal hydroxide in an alcoholic solution. A preferred embodiment is shown in the following reaction scheme. Trifluoroacetylation of Amine then Propargylation:

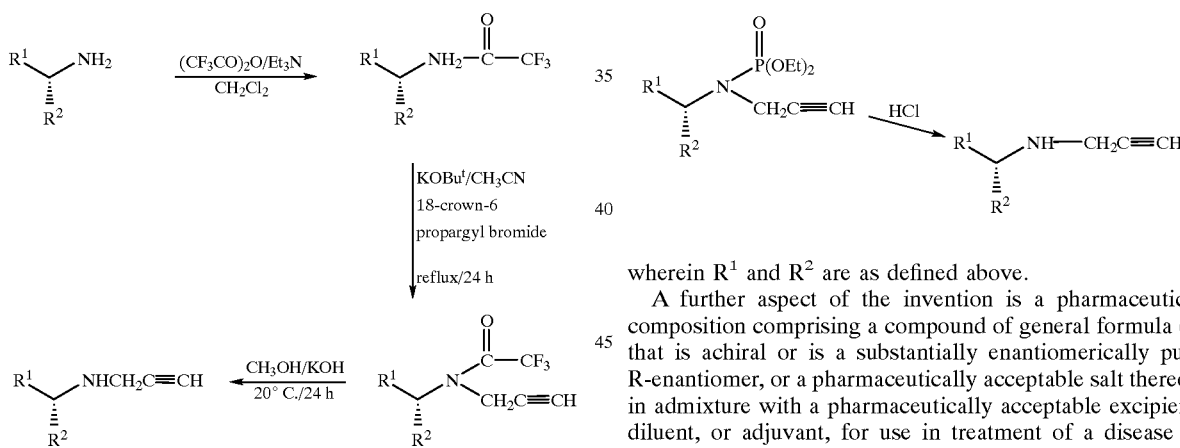

wherein $R^1$ and $R^2$ are as defined above.

Compounds of formula (I) can also be prepared by (c) reacting a compound of formula (V)

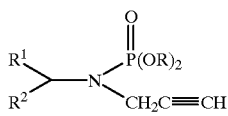
(V)

wherein $R^1$ and $R^2$ are as defined above and R is lower alkyl preferably ($C_1$–$C_2$) alkyl, with an acid.

The compound of formula V can be obtained by phosphorylating and then propargylating an amine. Again, the amine can be a racemate but is preferably a substantially pure enantiomer. An amine of formula (II) is reacted with a dialkylphosphite, for example diethyl or dimethyl phosphite, preferably in an organic solvent such as carbon tetrachloride, in the presence of an aqueous hydroxide, such as NaOH, and in the presence of a phase transfer catalyst such as benzyltriethylammonium chloride or tetrabutyl ammonium hydrogen sulfate.

The phosphorylated amine is then reacted with a propargyl compound of formula (III), preferably in the presence of aqueous base, such as NaOH, in the presence of a phase transfer catalyst, such as tetrabutyl ammonium hydrogen sulfate or benzyltriethylammonium chloride.

Thereafter it is acidified, to remove the phosphite moiety. A preferred embodiment of this process is set forth below.

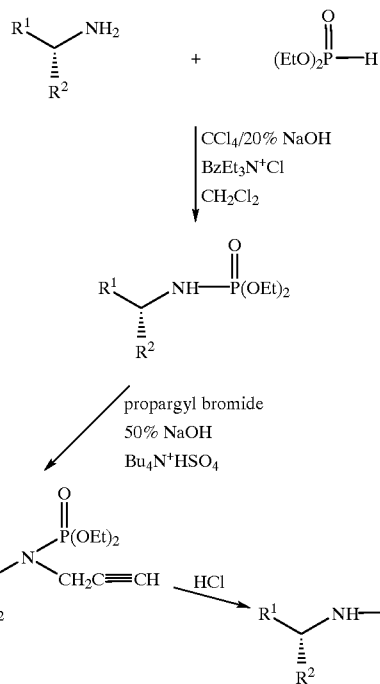

wherein $R^1$ and $R^2$ are as defined above.

A further aspect of the invention is a pharmaceutical composition comprising a compound of general formula (I) that is achiral or is a substantially enantiomerically pure R-enantiomer, or a pharmaceutically acceptable salt thereof, in admixture with a pharmaceutically acceptable excipient, diluent, or adjuvant, for use in treatment of a disease in which cell death occurs by apoptosis.

Yet a further aspect of the invention is a commercial package containing as active ingredient a compound of formula (I) that is achiral or is a substantially enantiomerically pure R-enantiomer, or a pharmaceutically acceptable salt thereof, together with instructions for its use for the treatment of disease in which cell death occurs by apoptosis.

Antiapoptosis and Neuroprotection Studies

The following biological data demonstrate that the compounds of the invention exhibit antiapoptotic and neuroprotective properties.

These data can be interpreted with the aid of the accompanying drawings, of which:

PHARMACOLOGICAL DATA

EXAMPLE I

In vitro Model of Rescue: Cerebellar Granule Cells

Effect of compounds of the invention for the prevention of apoptosis in cerebellar granule cells.

Cultures of cerebellar granule cells (CGC) can be induced into apoptosis by the addition of a high concentration of cytosine arabinoside (Ara C) (Dessi et al., 1995) and it has been shown that this is a p53 dependent apoptosis (Enokido et al, 1996). We have measured the antiapoptotic effect of N-(2-heptyl)propargylamine (2HPA) using this system and compared the results to those obtained with previously known aliphatic methyl propargylamines and deprenyl.

Cultures of CGC were obtained from 6–8 day old Wistar rat pups. Cultures were grown on glass in 35 mm petri dishes for 3 days and then used for experiments. 20 µl aliquots of drug solutions (Ara C, anti-apoptotic drugs, drug vehicles) were added to the medium of the cultures. 24 Hours later the cultures were fixed with FAM, and stained with bis-benzamide. Normal and apoptotic nuclei were counted to a total of 90–120 cells per culture. The optimum concentration of Ara C was found to be 100 µM. Concentrations in excess of 150 µM caused detachment of the cultures.

Figure 1A:
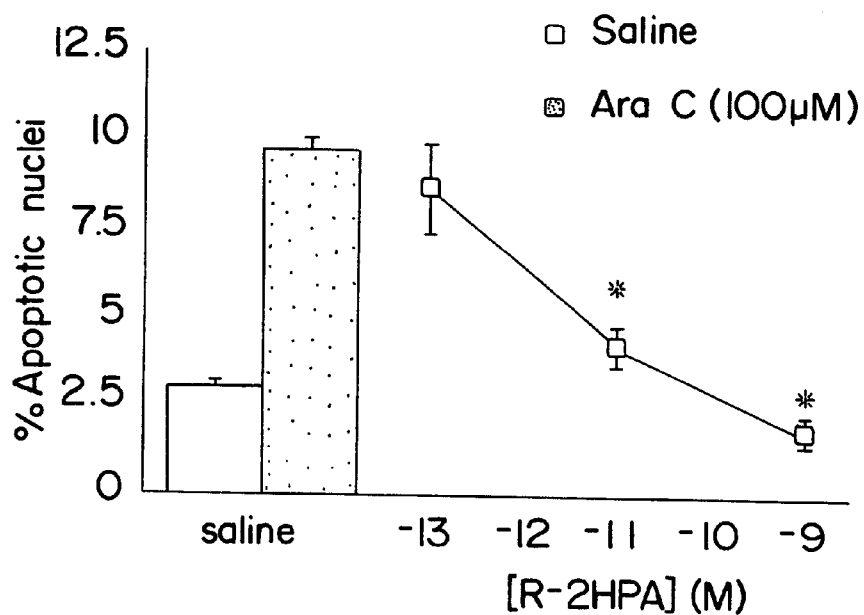
FIG. 1a is a graph showing the dose-response relationship of inhibition by R-N-(2-heptyl)propargylamine (R-2HPA) of Ara C induced apoptosis.
Figure 1B:
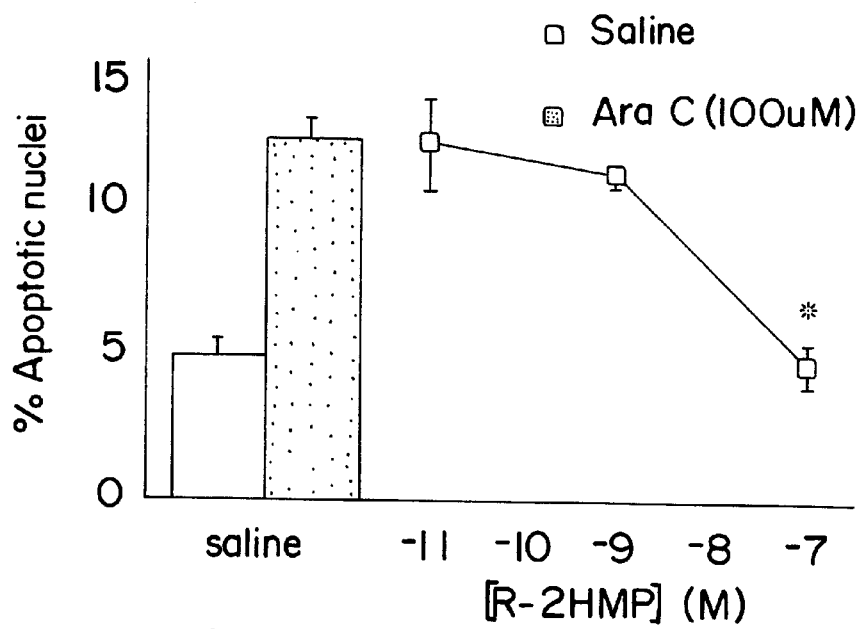
FIG. 1b is a graph showing the dose-response relationship of inhibition by (R)-N-(2-heptyl)-N-methyl-propargylamine (R-2HMP) of Ara C induced apoptosis.
Figure 1C:
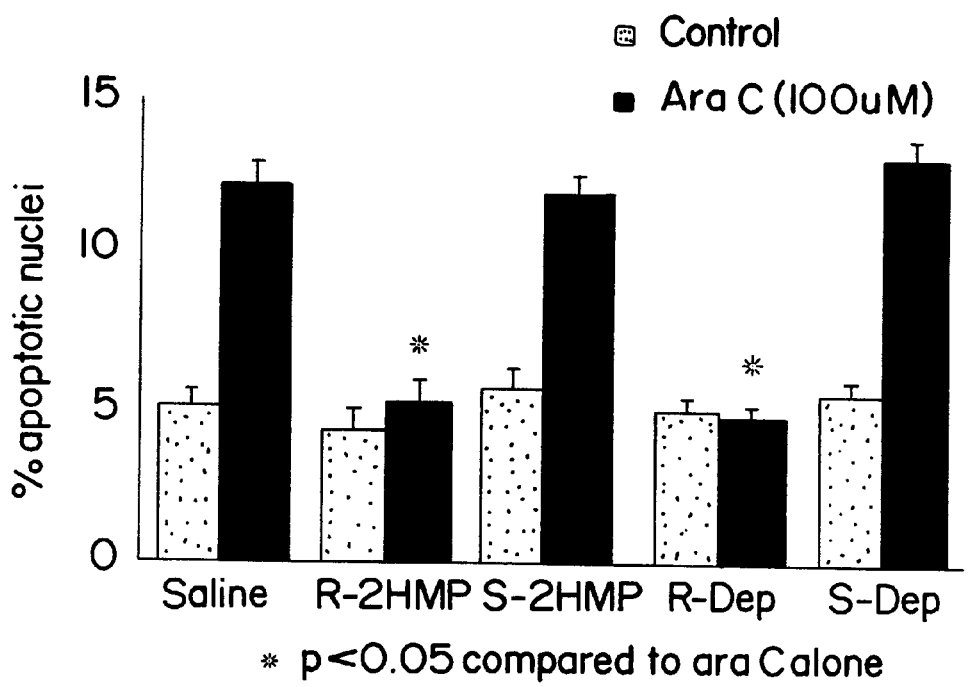
FIG. 1c is a graph showing the effect of R-2HMP, S-2HMP, R-deprenyl and S-deprenyl (all $10^{-7}$M) on Ara C induced apoptosis.
Figure 1D:
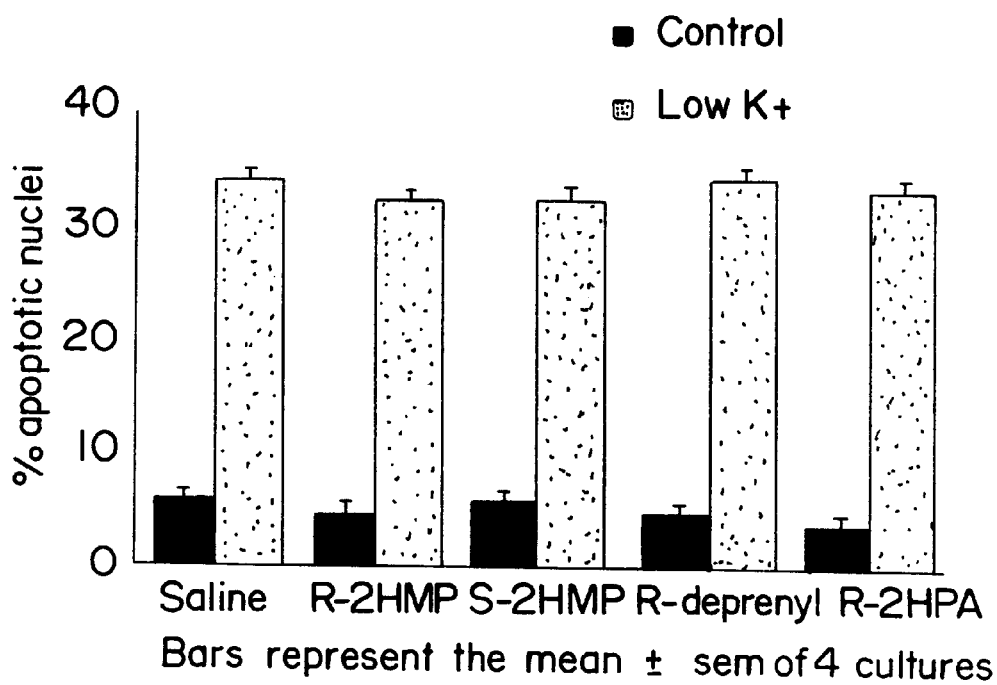
FIG. 1d is a graph showing that anti-apoptotic compounds do not prevent apoptosis in cerebellar granule cells induced by low concentrations of $K^+$ in the medium.

R-2HPA had an $EC_{50}$ of about $10^{-11}$ M (FIG. 1a). In contrast (R)-N-(2-heptyl)-N-methyl-propargylamine(R-2HMP) had an $EC_{50}$ between $10^{-9}$ and $10^{-7}$ M (FIG. 1b). In addition we have demonstrated the stereospecific effect of the R-isomers using aliphatic methyl propargylamines (R-2HMP and S-2HMP) and deprenyls (R-deprenyl and S-deprenyl) (FIG. 1c). R-2HMP and R-deprenyl ($10^{-7}$M) completely blocked the Ara C induced apoptosis while S-2HMP and S-deprenyl ($10^{-7}$M) did not (FIG. 1c). From Table 1 one can confirm that S-2HPA does not have an anti-apoptotic effect. None of these compounds prevented the P53 independent apoptosis that was induced by lowering the concentration of potassium (D'Mello, et al, 1993) in the medium (FIG. 1d).

It is concluded that Ara C induced apoptosis in cultures of CGC can be blocked by the aliphatic secondary propargylamines of the invention. From the comparison of the effect of the novel compound 2HPA versus that of previously reported 2HMP it is clear that the potency of the aliphatic secondary propargylamines of the invention in the prevention of p53 dependent apoptosis is much greater than the potency of the related known aliphatic methyl propargylamines. The rescue is stereospecific, the S-isomer having no anti-apoptotic effect. Further examination has shown that the S-enantiomers are in fact antagonists of the anti-apoptotic action of the R-enantiomers (lines Ara C+R-2HMP+S-2HMP and Ara C+R-2HMP+S-2HPA of Table 1).

TABLE 1

(S)-N-(2-heptyl)-N-methyl-propargylamine (S-2HMP) and (S)-N-(2-heptyl)-propargylamine (S-2HPA) antagonistic effect on antiapoptotic action of (R)-N-(2-heptyl)-N-methyl-propargylamine (R-2HMP)

| Treatment | Percent Apoptotic Nuclei |
|---|---|
| Control | 4.2 ± 0.3 |
| Ara C | 14.6 ± 0.9 |
| Control + R-2HMP | 4.8 ± 0.7 |
| Ara C + R-2HMP | 6.3 ± 0.8* |
| Control + S-2HMP | 5.0 ± 0.6 |
| Ara C + S-2HMP | 13.7 ± 1.1 |
| Ara C + R-2HMP + S-2HMP | 15.1 ± 0.9# |
| Control + S-2HPA | 4.7 ± 0.7 |
| Ara C + S-2HPA | 14.2 ± 0.9 |
| Ara C + R-2HMP + S-2HPA | 13.8 ± 1.2# |

Values represent the mean ± sem of 4 cultures.
Compounds were added at the following concentrations: Ara C, 100 µM, R-2HMP, 100 nM; S-2HMP, 10 µM; S-2HPA, 10 µM.
*P < 0.05 compared to Ara C alone.
P < 0.05 compared to Ara C + R-2HMP.

EXAMPLE II

Hypoxia/ischaemia Model

Apoptosis of hippocampal pyramidal neurons can be induced in vivo using a rat model of hypoxia/ischaemia (Paterson et al., 1996). This model produces selective, unilateral lesioning of the pyramidal neurons in the hippocampus which involves neuronal apoptosis.

This is demonstrated by the results obtained using a compound of the invention N-(2-heptyl)propargylamine (2-HPA). Previously reported (R)-N-(2 heptyl)-N-methyl-propargylamine has an $ED_{50}$ between 1 and 10 nmol/kg following subcutaneous administration. These two compounds, and the compounds (R)-N-(2-heptyl)-methylamine and R-(2-heptyl) amine were tested. Most active is R-2HPA (Table 2) and of the other compounds only R-2HMP shows significant activity. The secondary amine (R)-N-(2-heptyl)-methylamine (R-2HMA), and the primary amine (R)-(2-heptyl)amine (R-2HA), neither increase nor decrease the CA1 neuronal death.

TABLE 2

The effect of amine compounds (0.1 µmol/kg, s.c.) on CA1 survival in the hypoxia/ischaemia model.

| Compound | R-isomer | S-isomer |
|---|---|---|
| N-(2-heptyl)-N-methyl-propargylamine (2HMP) | 239 ± 35** | 112 ± 23 |
| N-(2-heptyl)-propargyl-amine (2HPA) | 320 ± 48** | 131 ± 19 |
| N-(2-heptyl)-methyl-amine (2HMA) | 85 ± 26 | — |
| (2-heptyl)-amine (2HA) | 90 ± 30 | — |

Values are the mean survival of CA1 neurons expressed as a percentage of vehicle treated controls (vehicle = 100%) ± sem (n = 6 – 10).
*P < 0.05,
**P < 0.01.

TABLE 3

The effect of oral administration of R-2HMP and R-2HPA on CA1 survival in the hypoxia/ischemia model

| Treatment | Percentage survival |
|---|---|
| Water | 100 ± 22 |
| R-2HMP | 112 ± 24 |
| R-2HPA | 230 ± 36* |

Values are means ± sem (n = 7 – 10) of CA1 survival relative to vehicle controls. Drugs given in a volume of 1 ml per animal, R-2HMP and R-2HPA at 0.1 mg/kg.
*p < 0.01 with respect to water.

Following oral administration of drugs the aliphatic propargylamine, R-2HPA, is more potent than its aliphatic methyl propargylamine analogue, R-2HMP (Table 3).

TABLE 4

The effects of a variety of aliphatic propargylamines (0.1 μmol/kg, s.c.) on CA1 survival in the hypoxia/ischaemia model.

| N-methyl-propargylamines | Percentage survival | Propargylamines | Percentage Survival |
|---|---|---|---|
| Branched-chain aliphatic propargylamines and methyl propargylamines | | | |
| R-2HMP | 239 ± 35** | R-2HPA | 320 ± 48** |
| S-2HMP | 112 ± 23 | S-2HPA | 131 ± 19 |
| R-2BuMP | 297 ± 52** | R-2BuPA | 263 ± 37** |
| S-2BuMP | 139 ± 38 | S-2BuPA | — |
| 2PrMP | 255 ± 43** | 2PrPA | 175 ± 20* |
| Straight chain aliphatic propargylamines and methyl propargylamines | | | |
| 1HxMP | 215 ± 24* | 1HxPA | 179 ± 23* |
| 1PrMP | 127 ± 31 | 1PrPA | 174 ± 29* |
| EMP | 82 ± 19 | EPA | 164 ± 18* |
| DMP | 117 ± 28 | MPA | 78 ± 31 |

Values are the mean survival of CA1 neurones expressed as a percentage of vehicle treated controls (vehicle = 100%) ± sem (n = 6–10).
*P < 0.05,
**P < 0.01.

Definition of abbreviations:
R/S-2HMP=(R)/(S)-N-(2-heptyl)-N-methylproparglamine,
R/S-2BuMP=(R)/(S)-N-(2-butyl)-N-methylpropargylamine,
2PrMP=N-(2-propyl)-N-methylpropargylamine,
R/S-2HPA=(R)/(S)-N-(2-heptyl)-propargylamine,
R/S-2BuPA=(R)/(S)-N-(2-butyl)-propargylamine,
2PrPA=N-(2-propyl)-propargylamine,
1HxMP=N-(1-hexyl)-N-methylpropargylamine,
1PrMP=N-(1-propyl)-N-methylpropargylamine,
EMP=N-ethyl-N-methylpropargylamine,
DMP=N,N-dimethylpropargylamine,
1HxPA=N-hexylpropargylamine,
1PrPA=N-propylpropargylamine,
EPA=N-ethylpropargylamine,
MPA=N-methylpropargylamine.

A variety of branched chain and straight chain aliphatic secondary propargylamines and their corresponding N-methyl analogues have been tested in the hypoxia/ischaemia model (Table 4). The data confirm that the secondary propargylamines are as efficacious as the aliphatic N-methyl propargylamines and that in the case of the branched chain compounds the process is stereospecific with the R-enantiomers being active and the S-enantiomers being inactive. The activities of the straight chain compounds, and of the non-chiral 2-propyl amines, N-(2-propyl)-N-methyl-propargylamine (2PrMP) and N-(2-propyl)-propargylamine (2PrPA), show that the chiral centre in the branched chain compounds is not required for activity in these latter compounds, although the activity appears to be slightly lower than those of the optimum branched chain compounds. Interestingly, 1PrMP was inactive but the analogue 1PrPA was active.

EXAMPLE III

Neuroprotective Effect of R-2HPA in Kainate Models

R-2HPA was found to be capable of preventing kainic acid-induced neuronal damage. Heat shock protein-70 (HSP70) and delayed c-Fos expressions have been found to be markers for neuronal injury following kainic acid-induced seizures (Zhang et al, 1996). The levels of both proteins were measured 24 h after a single injection of kainate (10 mg/Kg,i.p). The levels (assessed by quantitative immunohistochemical imaging) can be seen in Table 5. R-2-HPA was able to block the expression of both genes in the rat hippocampal CA1 region. This suggests that this compound can rescue these neurons.

TABLE 5

Effect of R-2-HPA on kainate-induced HSP70 and delayed c-Fos expression in rat hippocampal CA1 field.

| Treatment | HSP70 | Delayed c-Fos |
|---|---|---|
| Kainate | 10.8 ± 3.1 | 18.0 ± 4.5 |
| Kainate + R-2HPA | 4.6 ± 2.0* | 4.5 ± 3.7* |

Values are means ± sem (n = 5)
Kainate (10 mg/Kg, i.p.); Rats with seizures between stages IV severe to V severe were used. R-2HPA (0.25 mg/Kg, s.c.) was administered 4 h after kainate injection; HSP70 and c-Fos expression were assessed 24 h after kainate treatment (for details of method please see Zhang et al, 1996). Statistics were performed using ANOVA followed by Newman-Keuls multiple comparisons.
*p < 0.01.

Inhibition in vitro of Monoamine Oxidase Activity

The inhibition of the rat liver mitochondrial monoamine A and B activity by R- and S-enantiomers of the compounds of the invention and of the previously reported aliphatic N-methylpropargylamines, (i.e. the corresponding N-methyl analogues) is shown in Table 6. The MAO-B inhibitory activities of the aliphatic propargylamines, i.e. N-(2-butyl)-propargylamine (2BuPA), N-(2-hexyl)-propargylamines (2HxPA) and N-(2-heptyl)-propargylamine (2HPA), are substantially reduced in comparison to those of the N-methyl compounds, N-(2-butyl)-N-methyl-propargylamine (2BuMP), N-(2-hexyl)-N-methyl-propargylamine (2HxMP) and N-(2-heptyl)-N-methyl-propargylamine (2HMP). The R-enantiomers of the aliphatic propargylamines are more active than the S-enantiomers.

TABLE 6

Inhibition of rat liver mitochondrial monoamine oxidase B activities by enantiomers of some aliphatic propargylamines and aliphatic N-methyl propargylamines in vitro

| Inhibitors* | PE (1.9 × 10$^{-5}$ M) IC$_{50}$ | Comparison to most effective MAO-B inhibitor in group |
|---|---|---|
| R-2BuMP | 1 × 10$^{-6}$ M | 100% |
| S 2BuMP | 2 × 10$^{-6}$ M | 50% |

TABLE 6-continued

Inhibition of rat liver mitochondrial monoamine oxidase B activities by enantiomers of some aliphatic propargylamines and aliphatic N-methyl propargylamines in vitro

| Inhibitors* | PE<br>$(1.9 \times 10^{-5}$ M)<br>$IC_{50}$ | Comparison<br>to most effective<br>MAO-B inhibitor in group |
|---|---|---|
| R-2BuPA | $7 \times 10^{-5}$ M | 1.4% |
| S-2BuPA | $5 \times 10^{-4}$ M | 0.2% |
| R-2HxMP | $3 \times 10^{-8}$ M | 100% |
| S-2HxMP | $7 \times 10^{-7}$ M | 4.3% |
| R-2HxPA | $4 \times 10^{-6}$ M | 0.8% |
| S-2HxPA | nm | — |
| R-2HMP | $3 \times 10^{-8}$ M | 100% |
| S-2HMP | $4 \times 10^{-6}$ M | 0.8% |
| R-2HPA | $4 \times 10^{-6}$ M | 0.8% |
| S-2HPA | $3 \times 10^{-5}$ M | 0.1% |

Results are the average of at least 2 independent triplicate experiments for each compound. β-Phenylethylamine was used as the MAO-B substrate. Enzyme activity was assessed using a radiometric method as previously described (Yu et al, 1992).

Inhibition in vivo of Monoamine Oxidase Activity

The acute effect on the brain MAO activities of R-2HPA and R-2HMP following intraperitoneal injection is shown in Table 7. R-2HPA exhibits a weaker inhibitory effect on the mouse brain MAO-B with the $ED_{50}$ value 20 fold higher than that of its parent compound R-2HMP, which is 2.5 fold more potent than R-deprenyl. None of the compounds inhibit MAO-A in vivo or in vitro.

TABLE 7

Effect of R-2HMP, R-2HPA and R-deprenyl on mouse brain MAO-B activities after intraperitoneal administration of the drugs

| Inhibitors* | PE<br>$(1.9 \times 10^{-5}$ M)<br>$IC_{50}$ (mg/Kg) | Comparison<br>to most<br>effective inhibitor |
|---|---|---|
| R-2HMP | 0.2 | 100% |
| R-2HPA | 4 | 5% |
| R-deprenyl | 0.5 | 40% |

Results are the average of two independent triplicate experiments for each i.p. dose. The doses were 0.5, 1, 2, 5, 10, 20 mg/Kg. Striata were dissected from the brain two hours after i.p. administration of the drugs. MAO-B activities were then determined immediately (Yu et al 1992). The values were estimated from dose-response curves.

Selective Gene Expression Regulation by R-2HPA Regulation of Superoxide Dismutase 1

R-Deprenyl has been proposed to possess neuroprotective effects and one of the proposed mechanisms is that R-deprenyl induces superoxidase dismutase (SOD) activity, which would result in the inactivation of singlet oxygen. The induction of free radicals with the succeeding cascade reactions of lipid peroxidation are known to cause neuronal damage. Regulation of SOD activity is involved in several different pathological situations, such as brain ischemia, aging, and neurodegenerative diseases.

PC12 cells were used to study the gene regulation of SOD (copper, zinc-dependent type, i.e. SOD1) by (R)-2-heptylpropargylamine (R-2HPA). Previous findings have shown that NGF, R-deprenyl and some aliphatic methylpropargylamines can induce SOD1 mRNA in a dose dependent manner (Li, et al., 1995). The data in Table 8 show that R-2HPA can also stimulate SOD1 gene expression and could therefore have anti-oxidant effects.

TABLE 8

Effect of 2-HPA on SOD1 levels in PC12 cells

| Treatment | % of Control |
|---|---|
| Control | 100 ± 20 |
| R-2HPA (1 μM) | 184 ± 41** |

Mean ± SD (n = 4).
**$p < 0.01$.

The SOD1 mRNA levels were detected by Northern Blots using total RNA from cultured PC12 cells treated with R-2HPA for 24 hours. The blots were hybridized with SOD1 cDNA probe labelled with $P^{32}dCTP$ and the auto radiographs were scanned by a Beckman spectrometer.

R-2HPA Down-regulates LNGFR in PC12 Cells

LNGFR, also called the p75 NGF receptor, is a 75 kDa transmembrane protein with an incompletely characterized function. p75 has some sequence similarity to the tumor necrosis factor receptors, Fas antigen, CD40 and Apo-1, all of which mediate cell death. p75 expression induces neural cell death constitutively when LNGFR is unbound. Mutant PC12 cells (LNGFR deficiency clone) better survive apoptosis induced by NGF or serum withdrawal than the wild type PC12 cells. Binding by NGF or monoclonal antibody, however, inhibits cell death induced by LNGFR. Thus expression of LNGFR may explain the dependence of some neural cells on NGF for survival (Rabizadeh et al, 1993).

A recent report using antisense technology also indicated that LNGFR mediates survival or death depending on the stage of sensory neuron development. In this study it was demonstrated that, in vitro, lowering the levels of LNGFR expression in sensory neurons with antisense oligonucleotides largely prevents the NGF-mediated survival of sensory neurons from embryonic day 12 and 15 mice but increases the survival of embryonic day 19 and postnatal day 2 sensory neurons in the absence of NGF. Thus LNGFR is required for NGF-mediated survival in neurons at the stage of target innervation but can mediate an apoptotic signal at a later stage of cell development (Barrett et al., 1994).

The higher level of LNGFR expression in the central nervous system occurs in the cholinergic neurons of the nucleus basalis of Meynert, the cells most severely affected in Alzheimer's disease. These cells continue to express normal or supranormal amounts of LNGFR mRNA and protein during the neuronal degeneration associated with Alzheimer's disease. In contrast, cholinergic cells of the brainstem that resemble those of the nucleus basalis morphologically do not express LNGFR, nor do they degenerate in Alzheimer's disease.

Data in Table 9 show that R-2HPA downregulated LNGFR mRNA, suggesting a possible mechanism for the protective effects of R-2HPA.

TABLE 9

Effect on LNGFR mRNA levels in PC12 cells

| Treatment | % of Control |
|---|---|
| Control | 100 ± 5.4 |
| R-2HPA (1 μM) | 68.8 ± 16.4** |

Mean ± SD (n = 4).
**p < 0.01.

The LNGFR mRNA levels were detected by Northern Blots using total RNA from cultured PC12 cells treated with R-2HPA for 24 hours. The blots were hybridized with LNGFR cDNA probe labelled with $P^{32}$ dCTP and the auto radiographs were scanned by a Beckman spectrometer.

References

Barrett G. L. and Bartless P. F. (1994) The p75 nerve growth factor receptor mediates survival or death depending on the stage of sensory neuron development. Proc. Natl. Aca. USA 91, 6501–6505.

D'Mello, S. R., Galli, C., Ciottie T., & Calissano, P.(1993). Induction of apoptosis in cerebellar granule neurons by low potassium: inhibition of death by insulin-like growth factor I and cAMP. Proc. Natl. Acad. Sci. USA, 90, 10989–10993.

Dessi, F., Pollard, H., Moreau, J., Ben-Ari, Y., & Chariaut-Marlangue, C. (1995), Cytosine arabinoside induces apoptosis in cerebellar neurons in culture. J. Neurochem., 64, 1980–1987.

Enokido, Y., Araki, T., Aizawa, S., & Hatanaka, H.(1996). P53 involves cytosine arabinoside induced apoptosis in cultured cerebellar granule neurons. Neurosci. Lett., 203, 1–4.

Grace, J. M., Kinter, M. T., & MacDonald, T. L. (1994). Atypical metabolism of deprenyl and its enantiomer(s)-(+)-N,α-dimethyl-N-propynylphenethylamine, by cytochrome P450 2D6. Chem. Res. Toxicol., 7,286–290.

Li, X-M., Qi, J., Juorio, A. V. and Boulton, A. A. (1995a) (−)-Deprenyl enhances NGF-induced changes in superoxidase dismutase mRNA in PC12 cells. Proceedings of the 15th Biennial Meeting of International Society for Neurochemistry, Kyoto, Japan, Jul. 2–7, 1995.

Rabizadeh S., Oh J., Zhong L., Yang J., Bitler C. M., Butcher L. L. and Bredesen D. E. (1993) Induction of apoptosis by the low-affinity NGF receptor. Science, 261,345–348.

Paterson, I. A. Barber, A. J., Gelowitz, D. L., & Voll, C. (1996). (−)-Deprenyl reduces delayed neuronal death of hippocampal pyramidal cells. Neurosci, Biobehav. Revs., 20, in press.

Yu, P. H. Davis B. A., & Boulton, A. A. (1992). Aliphatic propargylamines: potent, selective, irreversible monoamine oxidase B inhibitors. J. Med. Chem., 35,3705–3713.

Zhang, X., Boulton, A. A., & Yu, P. H. (1996). Expression of heat shock protein-70 and limbic seizure-induced neuronal death in the rat brain. Eur. J. Neurosci, 8, 1432–1440.

Detailed Synthetic Procedures

The following non-limiting examples of synthetic procedures are provided.

EXAMPLE 1

(R)-N-2-Heptylpropargylamine hydrochloride [(R)-N-2-propynyl-2-heptanamine]

(R)-2HPA.HCl

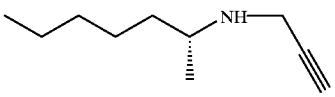

To a solution of (R)-2-heptylamine(98.6% R)(11.1 g,96.6 mmol) in anhydrous diethyl ether (165 ml) was added an 80% toluene solution of propargyl bromide (Lancaster Synthesis Inc., Windham, N.H., USA) (5.38 ml, 48.3 mmol). The solution was stirred under gentle reflux for 3 days. To the cold reaction solution was added 4N HCl (75 ml) and the mixture was evaporated to dryness under reduced pressure at 70° C. The red-orange viscous residue was basified by the addition of 20% NaOH, saturated with NaCl and then extracted with ether (3×30 ml). The combined extracts were dried over $MgSO_4$ then concentrated under reduced pressure at 30° C. The product was distilled under reduced pressure (water aspirator: 30 mm). Two fractions were collected: b.p. 55–74° C., 4.3 g=78% (of excess) [(R)-2-heptylamine] and b.p. 98–110° C., 4.3 g=58% [(R)-2-heptylpropargylamine] (based on 48.3 mmol propargyl bromide; 48% if based on 96.6 mmol (R)-2-heptylamine minus 37.4 mmoles recovered). The addition of 25% ethanolic HCl to an ether solution of the free base and cooling in a freezer for several hours resulted in the precipitation of the hydrochloride salt. m.p.=78.5–80° C. The optical purity was assessed by adapting the method of Durden et al (1997) for 2-alkylpropargylamines (%R=99.2).

Mass spectrum: m/e: 153 (M+); 138 (M—$CH_3$); 82 (base peak).

1H-NMR ($D_2O$, 300 MHz): 0.73 (t,3H); 1.17(d,3H); 1.1–1.3(m,6H); 1.43(m,1H);1.59(m,1H); 2.82(t,1H); 3.32 (m,1H); 3.79(t,2H).

Elemental Analysis: Calc: %C=63.30; %H=10.63; %N=7.38. Found: %C=63.56; %H=10.49; %N=7.15.

The starting material, (R)-2-heptylamine, was prepared as follows:

Racemic 2-heptylamine was resolved by repeated recrystallizations of its L-tartrate salt from methanol according to the method of Mazur (1970). Seven recrystallizations using a ratio of volume of methanol to weight of tartrate salt of 2.4 to 2.6 (increasing as the optical purity increased) gave the R-enantiomer with a purity of 98.6%R. In a separate experiment, after nine recrystallizations, the optical purity was 99.7%R. The optical purity was determined by derivatization with the chiral reagent(S)-N-trifluoroacetylprolyl chloride and then gas chromatography on a chiral column to resolve the diastereomers. (Durden et al., 1997).

EXAMPLE 2

(R)-N-2-Heptylpropargylamine hydrochloride[(R)-N-2-propynyl-2-heptanamine]

(R)-2HPA.HCl

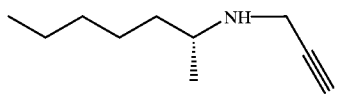

Crude (R)-N-trifluoroacetyl-N-2-heptylpropargylamine (7.3 g) was dissolved in 2N methanolic KOH (70 ml) and stirred at room temperature for 2 days. The reaction mixture was cooled in an ice-water bath and acidified with 20% methanolic HCl (75 ml). The precipitated KCl was filtered, washed with a little methanol and the combined filtrates were evaporated to dryness. The residue was basified with 10% NaOH(50 ml), saturated with NaCl and extracted with ether (2×25 ml). After drying over $MgSO_4$, most of the solvent was removed by rotary evaporation at 30° C. The residue (3.0 g) was distilled at 30 mm (water aspirator) to give a clear colourless liquid (boiling range 132–150° C.), 1.90 g. The hydrochloride salt was prepared as described in Example 1, Method 1.

Melting point, mass spectrum and 1H-NMR; as above (Example 1, Method 1).

The starting material, (R)-2-Heptylamine, was prepared according to Example 1.

(R)-N-Trifluoroacetyl-2-heptylamine

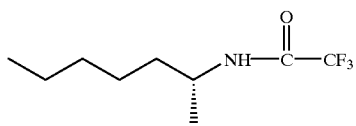

To a stirred ice-cold solution of (R)-2-heptylamine (3.5 g, 30 mmol) in chloroform (35 ml) and pyridine (6 ml) was added dropwise trifluoroacetic anhydride (6 ml, 38 mmol). After completion of the addition the solution was stirred overnight at room temperature. The solution was washed successively with 10% citric acid (3×15 ml) and saturated aqueous sodium bicarbonate solution (2×20 ml). The organic solution was dried over $Na_2SO_4$, filtered and the solvent was removed under reduced pressure at 40° C. The residue was a yellow liquid obtained in quantitative yield.

Mass spectrum: m/e: 211(M+);196(M—$CH_3$); 140(base peak).

(R)-N-Trifluoroacetyl-N-2-heptylpropargylamine

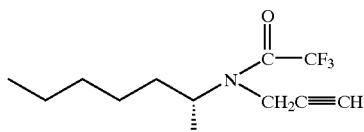

To a solution of N-trifluoroacetyl-N-2-heptylamine(6.33 g, 30 mmol) in $CH_3CN$ (75 ml)/t-butanol(0.5 ml) was added 18-crown-6(300 mg) and powdered potassium t-butoxide (3.36 g, 30 mmol). After stirring for 15 min most of the solids had dissolved and propargyl bromide (80% in toluene) (3.5 ml, 31.5 mmol) was then added dropwise. The solution was stirred at 80–85° C. (oil bath temperature) for 24 h during which time the solution became brown in color and a white solid precipitated. After the reaction mixture had cooled to room temperature, dichloromethane (75 ml) was added and the solids were filtered with suction and washed with dichloromethane. The weight of the solids (KBr) was 3.6 g (theoretical: 3.57 g). The combined filtrates were rotary evaporated to give 7.3 g of a dark brown liquid (theoretical yield=7.47 g). The product was not purified but used directly in the next step.

Mass Spectrum: m/e:249(M+);234(M—$CH_3$);178(base peak);140;39.

EXAMPLE 3

N-2-Propylpropargylamine hydrochloride [N-2-propynyl-2-propanamine]

2PrPA

The hydrochloride salt precipitated immediately on addition of HCl: m.p.=188.5–189° C.

Mass Spectrum:m/e:97(M+); 82(M—$CH_3$)(base peak).

1H-NMR ($D_2O$, 300 MHz): 3.77(d,2H); 3.41(m,1H); 2.81(t,1H); 1.19(d,6H).

EXAMPLE 4

(R)-N-2-Butylpropargylamine hydrochloride[(R)-N-2-propynyl-2-butanamine]

(R)-2BuPA

The starting (R)-2-butylamine(93.1%R) was purchased from Aldrich Chemical Co., Milwaukee, Wis., USA. The hydrochloride salt of 2BuPA precipitated immediately on addition of HCl: m.p.=136–137° C. Optical purity=98.4% R Mass Spectrum: m/e: 111(M+); 96(M—$CH_3$); 82(base peak).

1H-NMR($D_2O$, 300 MHz): 3.79(d,2H); 3.24(m,1H); 2.81 (t,1H); 1.65(m,1H); 1.45(m,1H); 1.17 (d,3H); 0.82 (t,3H).

EXAMPLE 5

(R)-N-2-Pentylpropargylamine hydrochloride [(R)-N-2-propynyl-2-pentanamine]

(R)-2PePA

The hydrochloride salt precipitated immediately on addition of HCl: m.p=107–108° C. Optical purity=99.5%R Mass Spectrum: m/e:125(M+); 110(M—$CH_3$); 82(base peak).

1H-NMR($D_2O$, 300 MHz): 3.78 (d,2H); 3.32(m,1H); 2.80(t,1H); 1.56(m,1H); 1.40($m_1$H); 1.23(m,2H); 1.15 (d,3H); 0.78(t,3H).

Elemental Analysis: Calc: %C=59.43; %H=9.98; %N=8.66. Found: %C=59.97; %H=9.26; %N=8.37.

EXAMPLE 6

(R)-N-2-Hexylpropargylamine hydrochloride[(R)-N-2-propynyl-2-hexanamine]

(R)-2HxPA

The hydrochloride salt precipitated on addition of HCl only after cooling in the freezer for several hours: m.p=96–97° C. Optical purity=97.1% R Mass Spectrum: m/e: 139(M+); 125(M—$CH_3$); 82(base peak).

EXAMPLE 7

(R)-N-2-Octylpropargylamine hydrochloride[(R)-N-2-propynyl-2-octanamine]

(R)-2OPA

The hydrochloride salt precipitated on addition of HCl only after cooling in the freezer for several hours: m.p.=78.5–79.5° C. Optical purity=99.4%R.

Mass Spectrum: m/e: 167 (M+); 152 (M—$CH_3$); 82 (base peak).

1H-NMR($D_2O$, 300 MHz): 3.80(d,2H); 3.30(m,1H); 2.81 (t,1H); 1.60(m,1H); 1.43(m,1H); 1.23(m,2H); 1.15(d+m, 11H); 0.71 (t,3H).

EXAMPLE 8

N-1-Propylpropargylamine hydrochloride[N-2-propynyl-1-propanamine]

1PrPA

The hydrochloride salt precipitated immediately on addition of HCl: m.p.=146–147° C.

Mass Spectrum: m/e:97(M+);68(base peak).

1H-NMR($D_2O$, 300 MHz): 3.79(d,2H); 2.98(t,3H): 2.85 (t,1H); 1.57(m,2H); 0.85(t,3H).

EXAMPLE 9

N-1-Butylpropargylamine hydrochloride[N-2-propynyl-1-butanamine]

1BuPA

The hydrochloride salt precipitated immediately on addition of HCl: m.p.=167–168° C.

Mass Spectrum: m/e:111(M+); 96(M—$CH_3$); 68(base peak).

1H-NMR ($D_2O$, 300 MHz): 3.75(d,2H); 3.00(t,3H); 2.81 (t,1H); 1.50(m,2H); 1.23(m,2H); 0.78 (t,3H).

EXAMPLE 10

N-1-Pentylpropargylamine hydrochloride [N-2-propynyl-1-pentanamine]

1PePA

The hydrochloride salt precipitated immediately on addition of HCl: m.p.=170–171° C.

Mass Spectrum: m/e: 125(M+); 110(M—$CH_3$); 68(base peak).

1H-NMR($D_2O$, 300 MHz): 3.79(d,2H); 3.02(t,3H); 2.83 (t,1H); 1.57(m,2H); 1.22(m,4H); 0.78(t,3H).

EXAMPLE 11

N-1-Hexylpropargylamine hydrochloride [N-2-propynyl-1-hexanamine]

1HxPA

The hydrochloride salt precipitated immediately on addition of HCl: m.p.=170–171° C.

Mass Spectrum: m/e: 139(M+); 125(M—$CH_3$); 68(base peak).

References

Durden, D. A.; Davis, B. A.; Boulton, A. A., (1997) "Enantioselective gas chromatographic assay of 2-alkylamines using N-(trifluoroacetyl) prolyl derivatives and a chiral capillary column." J. Chromatography B 689:165–173.

Mazur, R. H. (1970). "Absolute configuration of 1-methylalkylamines." J. Organic Chemistry 35: 2050–2051

What is claimed is:

1. A composition for the treatment of a disease in which cell death occurs by apoptosis, which composition comprises an effective amount of a compound having the formula I:

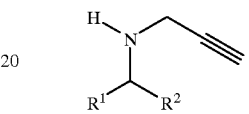

(I)

wherein $R^1$=H, $CH_3$ $R^2$=$CH_3(CH_2)_n$ and n represents an integer in the range from 0 to 16, with the provisos that (i) if $R^1$ is H, then n is not 4 or less;

(ii) if $R^1$ is $CH_3$ then n i s not 0; and (iii) if $R^1$ is $CH_3$ and n is 1 or 4, then the compound of formula (I) is in the form of a substantially pure enantiomer; or a pharmaceutically acceptable salt thereof, in admixture with a pharmaceutically acceptable carrier, excipient or adjuvant.

2. A composition according to claim 1, wherein said compound of formula I is selected from the group consisting of:

N-(1-heptyl)propargylamine;
N-(1-octyl)propargylamine;
N-(1-nonyl)propargylamine;
N-(1-decyl)propargylamine;
N-(1-undecyl)propargylamine:
N-(1-dodecyl)propargylamine;
R-N-(2-butyl)propargylamine;
R-N-(2-pentyl)propargylamine;
R-N-(2-hexyl)propargylamine;
R-N-(2-heptyl)propargylamine;
R-N-(2-octyl)propargylamine;
R-N-(2-nonyl)propargylamine.
R-N-(2-decyl)propargylamine,
R-N-(2-undecyl)propargylamine;
R-N-(2-dodecyl)propargylamine:

or a pharmaceutically acceptable salt thereof.

3. A composition according to claim 2, wherein the compound of formula (I) is in the form of a hydrochloride salt.

4. A method for the treatment of acute and chronic diseases in which cell death occurs by apoptosis or for the treatment of premature degeneration of cells in mammalian subjects, said method comprising administering to a patient in need thereof an effective amount of a compound having the formula I:

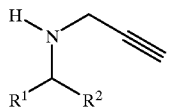 (I)

wherein $R^1$=H, $CH_3$;

$R^2$=$CH_3(CH_2)_n$;

and n represents an integer in the range from 0 to 16 provided that if R1 is methyl and R2 is not methyl the compound of formula (I) is in substantially enantiomerically pure form in the R-configuration, or a pharmaceutically acceptable salt thereof.

5. A method according to claim 4 wherein the disease is stroke, head trauma, Bell's palsy, spinal cord injuries, Alzheimer's disease, Parkinson's disease, Pick's multiple sclerosis, cardiac myopathies, nephropathy, retinopathy, diabetic complications, glaucoma, and idiopathic neuropathies.

6. A method according to claim 4 or 5, wherein said compound of formula I is selected from the group consisting of:

N-(ethyl)propargylamine;
N-(1-propyl)propargylamine;
N-(2-propyl)propargylamine;
N-(1-butyl)propargylamine;
N-(1-pentyl)propargylamine;
N-(1-hexyl)propargylamine;
N-(1-heptyl)propargylamine;
N-(1-octyl)propargylamine;
R-N-(2-butyl)propargylamine;
R-N-(2-pentyl)propargylamine;
R-N-(2-hexyl)propargylamine;
R-N-(2-heptyl)propargylamine;
R-N-(2-octyl)propargylamine;

or a pharmaceutically acceptable salt thereof.

7. A method according to claim 6, wherein the compound of formula (I) is in the form of a hydrochloride salt.

8. A commercial package for the treatment in mammals of acute and chronic diseases in which cell death occurs by apoptosis, or for the treatment of premature degeneration of cells in mammalian subjects, said package comprising a pharmaceutical agent having the formula (I), as defined in claim 4, together with instructions for use in the treatment of diseases in which cell death occurs by apoptosis, or for the treatment of premature degeneration of cells in mammalian subjects.

* * * * *

UNITED STATES PATENT AND TRADEMARK OFFICE
CERTIFICATE OF CORRECTION

PATENT NO. : 6,251,950 B1
DATED : June 26, 2001
INVENTOR(S) : Durden et al.

It is certified that error appears in the above-identified patent and that said Letters Patent is hereby corrected as shown below:

<u>Column 19,</u>
Line 3, after "Pick's", insert the following: -- disease, amyotrophic lateral sclerosis, Huntington's disease, --

Signed and Sealed this

Twenty-first Day of May, 2002

Attest:

JAMES E. ROGAN
*Director of the United States Patent and Trademark Office*

*Attesting Officer*

US006251950C1

(12) EX PARTE REEXAMINATION CERTIFICATE (5051st)
United States Patent
Durden et al.

(10) Number: US 6,251,950 C1
(45) Certificate Issued: Jan. 4, 2005

(54) ALIPHATIC PROPARGYLAMINES AS CELLULAR RESCUE AGENTS

(75) Inventors: David Durden, Saskatchewan (CA); Alick Paterson, Saskatchewan (CA); Bruce Davis, Saskatchewan (CA); Lillian Dyck, Saskatchewan (CA); Peter Yu, Saskatchewan (CA); Xinmin Li, Saskatchewan (CA); Alan Boulton, Saskatchewan (CA)

(73) Assignee: University of Saskatchewan Technologies Inc., Saskatoon Saskatchewan (CA)

Reexamination Request:
No. 90/006,624, Feb. 20, 2003

Reexamination Certificate for:
Patent No.: 6,251,950
Issued: Jun. 26, 2001
Appl. No.: 09/110,548
Filed: Jul. 6, 1998

Certificate of Correction issued May 22, 2002.

Related U.S. Application Data

(62) Division of application No. 08/891,904, filed on Jul. 14, 1997, now Pat. No. 5,840,979.

(51) Int. Cl.[7] .............................................. A61K 31/13
(52) U.S. Cl. .................... 514/671; 564/504; 564/509
(58) Field of Search ........................ 514/671; 564/409

(56) References Cited

U.S. PATENT DOCUMENTS 5,508,311 A  4/1996  Yu et al.

FOREIGN PATENT DOCUMENTS

FR    1 453 844    12/1966

OTHER PUBLICATIONS

Martin, Y.C. et al, "Regression Analysis of the Relationship Between Physical Properties and the In Vitro Inhibition of Monoamine Oxidase by Propynylamines" Journal of Medicinal Chemistry, Jan. 1, 1975, pp. 883–888, vol. 18, No. 9.

Podobaev, N. I. et al, "Acetylenic compounds as corrosion inhibitors in acid solutions", Chemical Abstracts, Aug. 21, 1967, Abstract No. 35421, vol. 67, No. 8.

Ben–Efraim, D.A., "The prototropic rearrangement of secondary propargylic amines", Tetrahedron, 1973, pp. 4111–4125, vol. 29.

*Primary Examiner*—Brian Davis

(57) ABSTRACT

The present invention relates to the use of a group of propargylamines of the general formula (I)

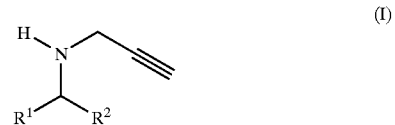

wherein $R^1$ is hydrogen or $CH_3$ and $R^2$ is $(CH_2)_n CH_3$ and n is an integer from 0 to 16, and salts thereof, as cellular rescue agents in the treatment and prevention of diseases in which cell death occurs by apoptosis. Some of the compounds of formula I are novel. The invention is also directed to the use of these compounds in the treatment of these diseases, as well as to processes for the preparation of the compounds.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 4–8 is confirmed.

Claims 1 and 2 are determined to be patentable as amended.

Claim 3, dependent on an amended claim, is determined to be patentable.

1. A composition for the treatment of a disease in which cell death occurs by apoptosis, which composition comprises an effective amount of a compound having the formula I:

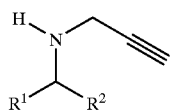

wherein
$R^1$=H, $CH_3$
$R^2$=$CH_3(CH_2)_n$
and n represents an integer in the range from 0 to 16, with the provisos that
  (i) if $R^1$ is H, then n is not [4] *5* or less;
  (ii) if $R^1$ is $CH_3$ then n is not 0; and
  (iii) if $R^1$ is $CH_3$ and n is 1 [or 4]–7, then the compound of formula (I) is in the form of a substantially pure enantiomer; or
a pharmacuetically acceptable salt thereof, in admixture with a pharmaceutically acceptable carrier, excipient or adjuvant.

2. A composition according to claim 1, wherein said compound of Formula I is selected from the group consisting of:
[N-(1-heptyl)propargylamine;]
N-(1-octyl)propargylamine;
N-(1-nonyl)propargylamine;
N-(1-decyl)propargylamine;
N-(1-undecyl)propargylamine;
N-(1-dodecyl)propargylamine;
R-N-(2-butyl)propargylamine;
R-N-(2-pentyl)propargylamine;
R-N-(2-hexyl)propargylamine;
R-N-(2-heptyl)propargylamine;
R-N-(2-octyl)propargylamine;
R-N-(2-nonyl)propargylamine.
R-N-(2-decyl)propargylamine,
R-N-(2-undecyl)propargylamine;
R-N-(2-dodecyl)propargylamine:
or a pharmaceutically acceptable salt thereof.

\* \* \* \* \*